United States Patent [19]

Ferris

[11] 4,323,073

[45] Apr. 6, 1982

[54] APPARATUS AND METHOD FOR CONTROLLING THE APPLICATION OF THERAPEUTIC DIRECT CURRENT TO LIVING TISSUE

[75] Inventor: Harold Ferris, St. Eugene, Canada

[73] Assignee: COS Electronics Corporation, Lyn, Canada

[21] Appl. No.: 68,431

[22] Filed: Aug. 21, 1979

[30] Foreign Application Priority Data

Sep. 11, 1978 [CA] Canada .................................. 311015

[51] Int. Cl.³ ............................................. A61N 1/20
[52] U.S. Cl. ............................................. 128/419 R
[58] Field of Search ................. 128/419 R, 421, 422, 128/420 R, 420 A, 423 R, 803

[56] References Cited

U.S. PATENT DOCUMENTS

| | | | |
|---|---|---|---|
| 2,555,037 | 5/1951 | Jensen | 128/803 |
| 3,185,939 | 5/1965 | Moss et al. | 128/422 |
| 3,645,267 | 2/1972 | Hagfors | 128/421 |
| 3,718,132 | 2/1973 | Holt et al. | 128/421 |
| 3,727,616 | 4/1973 | Lenekes | 128/422 |
| 3,964,477 | 6/1976 | Ellis et al. | 128/803 |
| 4,018,218 | 4/1977 | Carlson et al. | 128/422 |

*Primary Examiner*—William E. Kamm
*Attorney, Agent, or Firm*—Laff, Whitesel, Conte & Saret

[57] ABSTRACT

Apparatus and a method for applying current of a particular form to bulk resistance means such a living tissue. The applied current is D.C. at a level so low as to generate voltage gradients within the bulk resistance such as to be substantially under nerve or muscle stimulation potential. Apparatus is provided to increase the current level at a first predetermined rate to a first level for a first period of time, to lower it to a second level for a longer period of time, then to lower it to zero at a second predetermined rate. When applied to painful living tissue substantial reduction or elimination of pain and inflamation has been found to occur.

23 Claims, 3 Drawing Figures

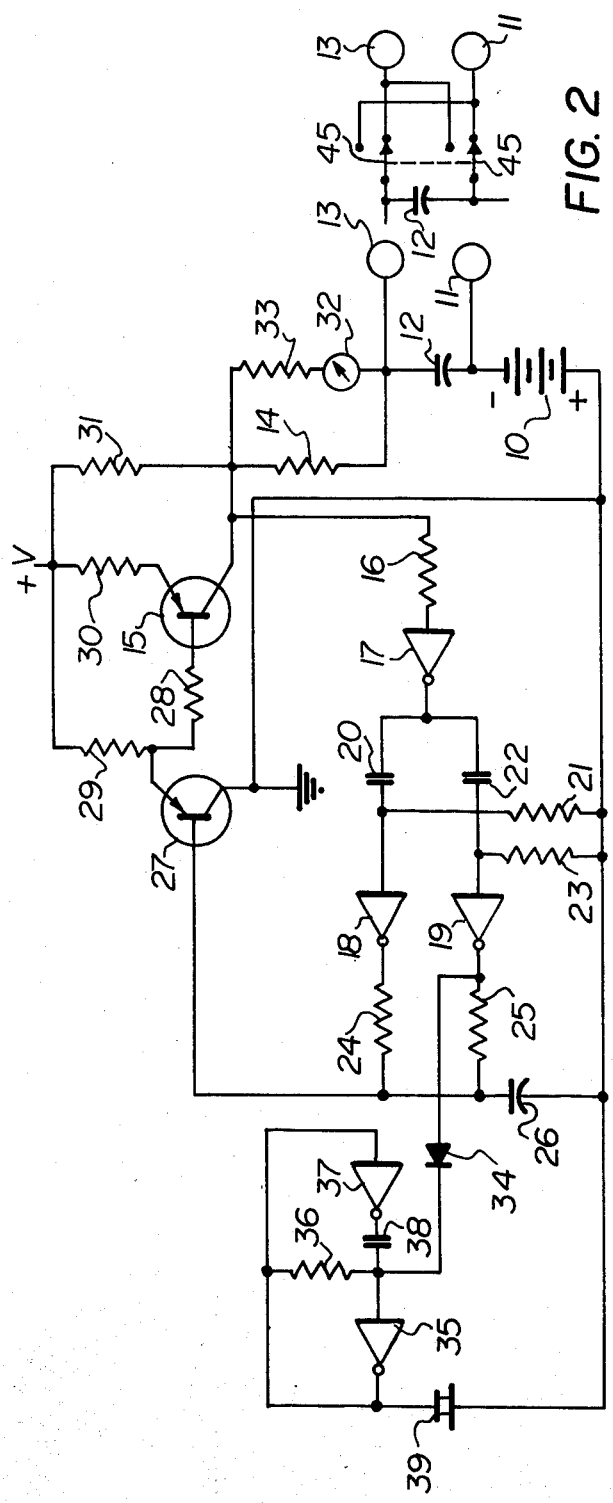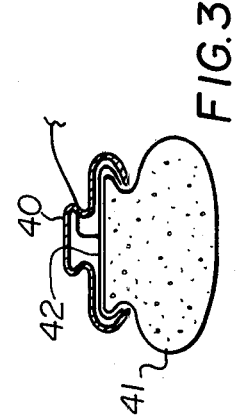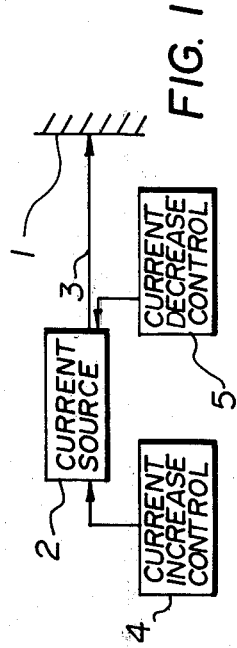

APPARATUS AND METHOD FOR CONTROLLING THE APPLICATION OF THERAPEUTIC DIRECT CURRENT TO LIVING TISSUE

INTRODUCTION

This invention relates to medical electronic apparatus and to a method for applying current to living tissue which includes muscle and nerves.

DESCRIPTION OF THE PRIOR ART

In the field of medical electronics, apparatus has been designed for applying current of various kinds to living tissue. In particular, apparatus had been used to apply stimuli to various locations on the body for the reduction of pain. Such apparatus typically applied pulse signals for reception by various pain receptor nerves; the pulse signal level applied being at a level which is somewhere between the nerve stimulation level and a higher "pain" level. It is believed that the nerves carry the pulse signal to an assemblage of nerve switching ganglia within the spine or at the base of the brain, causing the ganglia, after a certain period of time, to raise their pain threshold transmission levels, thus blocking nerve impulses transmitted from localized pain centers within the body from being passed to the brain.

It should be noted that the electrical pulses of the applied signals are relatively high, and are certainly greater than the nerve excitation level. Nerve standing potentials typically are of the order of 1/10 of a volt over approximately 500 angstroms, which translates to a gradient of the order of 20,000 volts per centimeter. Applied pulse signal potential gradients are thus significant relative to of this level to stimulate nerve impulses to the aforenoted ganglia.

Further, muscle standing potentials across muscle membranes are typically 50–60 millivolts. It is believed that application of the aforenoted pulse signals to the body is highly uncomfortable, since muscles and nerves are stimulated, and the body experiences the feeling of electrical shock, albeit localized.

In the publication *ADVANCES OF NEUROLOGY*, VOL. 4, Raven Press, New York, 1974, the articles "TREATMENT OF PAIN BY CHANGING THE ACID-BASE BALANCE," p. 559ff and "PAIN—A GENERAL CHEMICAL EXPLANATION," p. 45ff Mr. Olov Lindahl, of the Orthopedic Center, Regionsjukhuset Linkoping, Sweden points out that most textbooks provide no actual explanation of pain, but only ascribe pain to mechanical, thermal, or chemical stimuli, and he puts forward a theory of the chemical nature of the source of pain. Mr. Lindahl wrote that it appeared to him that pain is elicited by chemical means, and particularly by an elevated hydrogen-ion concentration in a nerve or in the vicinity of a nerve or nerve ending. Mr. Lindahl wrote further that he successfully treated pain by reducing the pH, i.e. by adjusting the pH of the human body. However, treatment appeared to take 2–3 days using his chemical approach.

In my early experiments concerning the present invention, I concluded that the "hydrogen-ion" theory of Lindahl as the source of pain was correct. Since the pressure of hydrogen-ions at the cell wall appeared to be the cause factor of pain, I called these ions "chemical messengers," as an analogy for nerve impulses carrying "electrical messages". In the disclosure below, the term "chemical messengers" designates the chemicals as cribed by Lindahl to cause pain, particularly hydrogenions.

BACKGROUND OF THE INVENTION

I have discovered that certain kinds of pain can be reduced or eliminated by the application of an entirely different form of current signal to painful areas of the body. Accordingly, I have invented an apparatus for application of such current, and a method of providing such current in the required useful form.

The apparatus of the invention provides means for applying direct current rather than pulsing signals at a low or at various low levels and at low rates of change. The current levels cause potential gradients to occur in the tissue which are substantially less than the nerve or muscle excitation potentials. Accordingly, there is not sensation of electrical shock, no nerve stimulation, and no spasm or other stimulation of muscle tissue. The current is specifically of the form which avoids the generation of nerve impulses, and consequently, no impulses are passed via nerves to the spine or brain.

It has been found that various kinds of pain are removed or eliminated, as well as certain kinds of inflammation which surrounds damaged tissues. The pain which is reduced or eliminated appears to involve healthy tissue which has received chemical messengers from the distressed cells. The present invention is believed to act to neutralize the chemical messengers, thus substantially reducing the region of affected distress message receivers, which thus do not respond and do not generate pain messages. Indeed, the chemical messengers are believed to be neutralized sufficiently that they do not reach the nerve dendrites, thus substantially reducing the probability that pain messages will be generated by the nerve and carried to the brain.

SUMMARY OF THE INVENTION

To provide the required form of direct current to living tissue, the apparatus of the invention is comprised of means for raising the current level passing through the tissue from a very low level or zero to a first predetermined higher level at a first controlled rate, means for maintaining the current level passing through the tissue at a second predetermined level for a first controlled time period following attainment of the first predetermined current level, and means for lowering the current level passing through the tissue to a very low level or zero at a second controlled rate following the first controlled time period.

Preferably the second predetermined level is sufficient to cause a voltage gradient in the tissue of less than about 50 millivolts per centimeter, and typically 10 millivolts per centimeter.

Since the tissue includes muscle and nerves, it will be immediately recognized that a gradient of 10 millivolts per centimeter is many orders of magnitude smaller than the standing potential of the nerve itself, which as noted above, was 20,000 volts per centimeter.

The invention is also a method of controlling direct current applied to a living tissue, comprising increasing the current from zero or a very low level to a first predetermined level at a first controlled rate, maintaining the first predetermined current level for a first period of time, and decreasing the current at a second controlled rate to a very low level or zero following the first period of time.

Current is applied and maintains the first level for a short period of time, and is then reduced to a lower current level for a longer period of time after which it is terminated at a controlled rate.

INTRODUCTION TO THE DRAWINGS

A better understanding of the invention will be obtained by reference to the detail description below, and to the following drawing, in which:

FIG. 1 is a block schematic of the invention,

FIG. 2 is a detailed schematic diagram of the invention, and

FIG. 3 is a cross-section of an electrode useful for applying current to living tissue.

DETAILED DESCRIPTION OF THE INVENTION

While the present invention is useful for applying direct current to living tissue, the specific invention is apparatus and a method for applying direct current at a controlled rate to certain kinds of living tissue, including tissues of animals.

Turning first to FIG. 1, a portion of living tissue 1 is shown in cross-section. Means for applying current at a controlled constant rate 2 is included, with a dual current path 3 applied against the tissue 1.

Means for raising the current level 4 is connected to the current source 2, as well as means for decreasing the current level 5.

Upon application of the current path 3 to tissue 1, the current from current source 2 is passed through the tissue from an initial zero level to a first predetermined higher level. The increase occurs at a first control rate. Since the rise time of the current is relatively long, current does not suddenly jump to a high level, and there is no differentiation thereof within bulk capacitance which might exist in the tissue which would otherwise give rise to a voltage sufficient to cause a nerve impulse to be generated. There is therefore no sensation of electrical shock or of current flow at the instant of application of current or during the period of current increase to the first predetermined higher level.

The current is then held at the first predetermined level for a first controlled time period. The level of current which is maintained should be sufficient to cause a potential gradient of less than about 50 millivolts per centimeter but preferably approximately 10 millivolts per centimeter within the tissue. While this gradient is not absolutely essential and various other current levels can be utilized for various kinds of tissue, the current level which is preferred to be maintained should be less than that required to cause a voltage gradient within the tissue sufficient to stimulate muscle membrane.

After maintaining the current level for a predetermined period of time, the current level is reduced to zero or to a very low level at a second controlled rate. The reduction of current during the second controlled rate is effected for similar reasons as the increase of current, i.e., the desire to eliminate the possibility of the stimulation of nerves or muscle tissue due to differentiation of the trailing edge of the current signal.

As noted above, preferably the voltage gradient in the tissue should be about 10 millivolts per centimeter, which is held for a period of between 10 and 60 seconds, although the period of 20 to 30 seconds has been found to be particularly useful. The rate of increase and decrease of the current can be approximately 20 milliamperes per second, although the present specific design provides the initial increase in current without dileterious effects during a period of $\frac{1}{4}$ to $\frac{1}{2}$ second.

In the preferred form of the invention, the current is increased to the first predetermined level at a rate of 5 milliamperes per second which is held for a period of time of about 5 to 10 seconds, following which it is lowered to a lower current level for about 25 seconds. The first higher current level typically can be about 5 milliamperes d.c., and the second current level typically can be about to 2 to $2\frac{1}{2}$ milliamperes d.c. The 5 milliamperes current, when applied to the human body has been calculated to provide a maximum voltage gradient of about 20 millivolts per centimeter, which, it will be noted, is less than the muscle stimulation voltage gradient.

Turning now to FIG. 2, a detailed schematic diagram of the apparatus of the present invention is shown. A battery 10 is connected with its positive terminal to ground and its negative terminal to an electrode 11, which negative terminal is also connected through capacitor 12 to electrode 13. Electrode 13 is connected through resistor 14 to the collector of a PNP transistor 15, and also through resistor 16 to the input of an inverting buffer 17.

The output of buffer 17 is connected through a pair of timing circuits to the inputs of inverting buffers 18 and 19. The timing circuit connected between the output of buffer 17 and the input of buffer 18 is comprised of series capacitor 20, and resistor 21 which is connected between the input of buffer 18 and ground.

The timing circuit connected between the output of buffer 17 and the input of buffer 19 is comprised of series capacitor 22, and resistor 23 which is connected between the input of buffer 19 and ground.

The outputs of buffers 18 and 19 are respectively connected through resistors 24 and 25 to one terminal of capacitor 26. The other terminal of capacitor 26 is connected to ground.

The junction of resistors 24 and 25 and capacitor 26 is connected to the base of PNP transistor 27. The collector of transistor 27 is connected to ground, and the emitter is connected through resistor 28 to the base of transistor 15, and through resistor 29 to a source of potential +V.

The emitter of transistor 15 is connected to source of potential +V through resistor 30 and its collector is connected to source of potential +V through resistor 31.

Resistor 14 is bypassed by a voltmeter 32 which is connected in series with resistor 33 for scaling purposes.

The output of buffer 19 is connected to the anode of a diode 34 which has its cathode connected to an oscillator as follows. The cathode is connected to an oscillator, i.e. to the input of an inverting buffer 35, which has its output connected back to its input through resistor 36. Its output is also connected to the input of inverting buffer 37, which has its output connected through capacitor 38 to the input of buffer 35. The output of buffer 35 is connected through a piezoelectric sounder 39 to ground.

Under steady-state non-operative conditions, the constant current amplifier formed by the circuitry involving transistors 15 and 27 is shut off, except for any leakage current which might be at microampere level, passing from potential source +V to ground. The input of buffer 17 is at a potential approaching +V.

As soon as electrodes 13 and 11 are applied to a bulk resistance, electrode 13 drops to low level approaching the potential at electrode 11 since it is now in a conductive path from the negative terminal of battery 10. Accordingly, the collector of transistor 15 goes to low level as does the input of buffer 17, due to the conductive paths through resistors 14 and 16. However, since transistor 15 is not yet turned on, insignificant current flows through the tissue to which electrodes 11 and 13 are applied.

With the input of inverting buffer 17 dropping to low potential level, its output goes to high level. Prior to this occurrence, however, the inputs of buffers 18 and 19 were at low potential level since they are connected directly to the ground through resistors 21 and 23. Since now the output of buffer 17 goes to high level, capacitors $C_1$ and $C_2$ begin charging. As they begin charging with an onrush of current, a potential drop is created across resistors 21 and 23, and the inputs of buffers 18 and 19 suddenly go to high level.

The time constant of capacitor 20 with resistor 21 in the present embodiment should be approximately 5 seconds, and the time constant of capacitor 22 with resistor 23 should be approximately 25 seconds. Accordingly, the output of inverting buffer 18 drops to low level for a period of approximately 5 seconds, and the output of inverting buffer 19 drops to low potential level for a period of about 25 seconds.

The output of buffers 18 and 19 are connected to the base of transistor 27 through individual resistors 24 and 25. Consequently, the base of transistor 27 is connected to the output of buffer 18 for 5 seconds and to the output of buffer 19 for 25 seconds, with the first 5 seconds of the latter simultaneous with the 5 seconds connection as noted above.

However, capacitor 26 which is of fairly large value such as 4.7 microfarads had been charged to a level approaching +V. With the provision of a discharge path through resistors 24 and 25 to the output of buffers 18 and 19 during the low level conduction periods of the latter, the capacitor voltage and therefore the base voltage of transistor 27 is modified as follows.

As soon as both buffers 18 and 19 are conductive and their outputs drop to low level, current from the charge held on capacitor 26 passes through resistors 24 and 25. The discharge time constant of capacitor 26 is approximately 0.25 seconds, assuming resistors 24 and 25 are each 100,000 ohms. Accordingly, the base of transistor 27 achieves a low level during the 0.25 second transition period.

However, after about 5 seconds, the output of buffer amplifier 18 returns to high level due to the charging time constant of capacitor 21. With buffer 19 output at low level and buffer 18 output at high level, the emitter follower transistor 27 base is driven to $+\frac{1}{2}V$.

Emitter follower 27 drives output transistor 15 having current negative feedback developed by resistor 30.

Once the 25 second period as noted above has expired, the output of buffer 19 goes to high level due to the charging time constant of capcitor 22. Accordingly, the potential across capacitor 26 and the base potential of transistor 27 rises, cutting off conduction of transistor 27. The time constant of charging of capacitor 26 thus control the rate of turnoff of transistor 27.

It will be seen that the transistor base voltage initially was high, and then dropped to a low level through a short controlled time period, and after about 5 seconds rose to an intermediate level. Further, after about a total elasped time of 25 seconds, the base potential rises to a high cutoff level.

The operation of transistor 27 is thus responsive. After initially being cut off, it begins conduction, increasing current conduction over the initial short controlled time period, to a maximum level which is controlled by the low base potential during the initial 5 interval. Collector current then decreases during the second 0.5 second transition period to an intermediate current level lower than the first level. Once the base voltage has again risen to its initial level, transistor 27 cuts off collector current.

In a well-known manner, transistor 15 operates responsively with transistor 27 as a constant current source. Collector current from transistor 15 passes through resistor 14, electrode 13, the bulk resistance, electrode 11, through battery 10, to ground, to which the collector of transistor 27 is connected.

The current passing through the tissue can be determined by measuring the voltage drop across resistor 14. A voltmeter comprising meter 32 in series with resistor 33 are connected in parallel with resistor 14 for this purpose.

It should be noted that for safety reasons, the circuit will not operate and continuously apply current following the expiry of the 25 second interval, should electrodes 11 and 13 be maintained in contact with the tissue. They must be removed from contact, allowing the circuit to return to steady-state, in which the input of buffer 17 has been raised to high level. After this has occurred, the electrodes may be reapplied to the tissue, whereupon current will be passed as described above for the aforenoted controlled periods and to the controlled levels.

Of course, an alternative circuit may use an on-off switch, as long as the controlled rise and fall times of the current are obtained.

In one embodiment capacitors 20 and 22 were respectively 4.7 microfarads and 22 microfarads, while resistors 21 and 23 were each 1.2 megohms. Resistor 16 was 2.5 megohms, resistor 14 was 1,000 ohms, resistor 31 was 1.2 megohms and potential +V was 4.5 volts. For biasing transistors 27 and 15, resistor 13 was 470 ohms, resistor 28 was 2,200 ohms, and resistor 29 was 6,800 ohms, and transistors 27 and 28 were of type 2N3905 and MPSU60.

The preferred embodiment of the invention employs an audio frequency oscillator comprised of buffers 35 and 37. Its frequency of oscillation is determined by capacitor 38 in series between the buffers and resistor 36 connected between the input of buffer 35 and its output, which is also connected to the input of buffer 37. Diode 34 couples the oscillator circuit from the input of buffer 35 to the output of buffer 19 so that in the quiescent state, buffer 19 output is high, forcing the input of buffer 35 high and thus preventing oscillation.

Since all buffers 17, 18, 19, 35, 37 are preferably CMOS devices, virtually no current is drawn by any of them during the quiescent state.

During the active state, the output of buffer 19 is at low level, removing the positive bias at the input of buffer 35 allowing the oscillator to function and drive the transducer 39, thus providing an aural signal. This indicates that current is being delivered to the electrodes 11 and 13.

If the external resistance between electrodes 11 and 13 is too high battery 10 cannot deliver the current required to keep the collector of transistor 15 out of saturation and consequently the voltage between collector and ground goes positive causing the base of emitter follower 27 to go positive and turn off the tone oscillator. Thus the operator is warned of this condition by hearing the oscillator tone output flutter on and off.

It has been found advantageous to be able to reverse the polarity of the electrodes during application of current to living tissue. Accordingly a double pole double throw polarity reversing switch 45 is shown in series with electrodes 11 and 13 in an alternate electrode connection arrangement to the right of the schematic diagram.

The cross-section of an electrode which may be used in this invention is shown in FIG. 3. A plastic handle 40 is shaped to retain a polyurethane foam sponge 41 therewithin. Surrounding the held portion of the sponge is a conductive layer 42 such as stainless steel. A wire 43 is in contact with conductive layer 42, which itself makes broad contact with sponge 41.

The sponge 41 is saturated with a saline water solution. A pair of the electrodes is utilized, one connected by wire 43 to electrode 11 and the other by a corresponding wire to electrode 13. During operation, the insulating handles of the electrodes are held by an operator, and are placed in contact at spaced locations on the tissue, on opposite sides of a wound. To make particularly good contact, the sponges may be rotated slightly to ensure that the saline solution attains intimate contact with the surface of the tissue.

This contact automatically turns on the apparatus causing automatic level adjustment of the current, and subsequent shutting off of the current as described earlier.

Where pain in living tissue has not been sufficiently removed, the electrodes may be placed at 90° to a line adjoining the previous locations of the electrodes, for a second application of current.

The present apparatus has been found to be a useful appliance for the application of direct current to living tissue, whereby it is believed chemical pain messengers are neutralized. It is also believed to show in certain instances neutralization to apparently reduce inflammation effects.

A person understanding this invention may now conceive of various alternatives, variations, or other embodiments. All are considered within the scope and sphere of the present invention as defined in the appended claims.

I claim:

1. Apparatus for controlling the application of therapeutic direct current to living tissue comprising:
    (a) means for increasing the amplitude of an applied direct current passing through the tissue from an insignificant level to a first predetermined higher level at a first controlled rate,
    (b) means for changing the current level passing through the tissue to a second predetermined lower level and maintaining it for a predetermined controlled time period following attainment of the first predetermined current level, and
    (c) means for decreasing the current level passing through the tissue to an insignificant level at a second controlled rate following the controlled time period,
    the current levels being such as to generate voltage gradients in the tissue which are less than nerve stimulation voltage gradients.

2. Apparatus as defined in claim 1, in which the means for changing the current level includes means for controlling the second predetermined level so as to provide a voltage gradient in the tissue up to about 50 millivolts per centimeter.

3. Apparatus as defined in claim 2 in which the first predetermined current level is higher than the second predetermined current level, including further means for maintaining the first current level for a preliminary controlled time period.

4. Apparatus as defined in claim 3, in which said first predetermined level of current is about 5 milliamperes and the second predetermined level of current is about 2½ milliamperes.

5. Apparatus as defined in claim 4, in which the preliminary controlled time period is about 5 seconds, and the predetermined controlled time period is between about 20 and 30 seconds.

6. Apparatus as defined in claim 4 or 5, in which said first controlled rate is about 5 milliamperes per second.

7. Apparatus as defined in claim 1, 2 or 5, further including electrode means for applying said current to said tissue through a broad surface contact therewith and having means for retaining conductive fluid material between the electrode means and the tissue.

8. Apparatus as defined in claim 1, 2 or 5, further including electrode means for applying said current to said tissue through a broad surface contact therewith and having means for retaining a saline water solution between the electrode and the tissue.

9. Apparatus as defined in claim 1, in which the means for changing the current level includes means for controlling the second predetermined level so as to provide a voltage gradient in the tissue of approximately 10 millivolts per centimeter.

10. Apparatus as defined in claim 1 in which the amplitude of first predetermined current level provides a voltage gradient in the tissue of about 20 millivolts per centimeter.

11. Apparatus as defined in claim 3 or 10 in which said first controlled rate is about 20 milliamperes per second.

12. Apparatus as defined in claim 3 or 10, in which said tissue includes a capacitive component, the apparatus further including means for controlling said rates so as to be slower than a predetermined rate whereby a derivative voltage is produced in said tissue by said capacitive component when said current is applied, which derivative voltage is less than nerve stimulation voltage and which is less than standing potential across muscle membrane.

13. Apparatus as defined in claim 1, in which the current levels are such as to generate voltage gradients in the tissue which are less than muscle membrane exciting voltage gradients.

14. A method of controlling direct current applied to living tissue comprising:
    (a) applying a direct current source to living tissue,
    (b) increasing the amplitude of the direct current from an insignificant level to a first predetermined level at a first controlled rate,
    (c) maintaining the first predetermined current level for a first period of time, and
    (d) decreasing the current at a second controlled rate to an insignificant level at a second controlled rate following the first period of time,
    the current which is applied being predetermined to generate voltage gradients in living tissue which are less than nerve stimulation voltage gradients.

15. A method as defined in claim 14 including raising the current to said first predetermined current level to cause a voltage gradient in the tissue of less than 50 millivolts per centimeter.

16. A method as defined in claim 14 including raising the current to said first predetermined current level to cause a voltage gradient in the tissue of approximately 20 millivolts per centimeter.

17. A method as defined in claim 14 including the step of decreasing the current level from the first current level to a second predetermined current level for a second period of time prior to said step of decreasing the current to said insignificant level.

18. A method as defined in claim 17 including raising the current to said first predetermined current level to cause a voltage gradient in the tissue of the order to 20 millivolts per centimeter, and reducing the current to said second predetermined current level to cause a voltage gradient in the tissue of about 10 millivolts per centimeter.

19. The method as defined in claim 17 in which the first period of time is in the range of about 5-10 seconds, and the second period of time is in the range of about 10-60 seconds.

20. A method as defined in claim 19 in which the first controlled rate is about 5 milliamperes per second.

21. A method as defined in claim 17, 18 or 19 in which the first predetermined current level is about 5 milliamperes and the second predetermined current level is about 2 milliamperes.

22. A method as defined in claim 17 including raising the current to said predetermined current levels to cause voltage gradients in living tissue which are below the standing voltage gradient across muscle membrane.

23. A method as defined in claim 17 in which said tissue includes a capacitive component, said method including controlling said rate whereby a derivative voltage is produced in said bulk resistance means by said capacitive component when said current is applied which is less than nerve stimulation voltage and which is less than the standing voltage gradient across muscle membrane.

* * * * *